United States Patent

Frede et al.

[11] Patent Number: 5,965,032
[45] Date of Patent: Oct. 12, 1999

[54] PURIFICATION OF α-, β- OR γ-SUBSTITUTED CARBOXYLIC ACIDS

[75] Inventors: Markus Frede, Eppelheim; Christian Dully, Ludwigshafen; Klaus Ditrich, Gönnheim; Johann-Peter Melder, Neuhofen; Hans-Jürgen Weyer, Bobenheim-Roxheim; Achim Weitze, Brunsbüttel, all of Germany

[73] Assignee: BASF Aktiengesellschaft, Ludwigshafen, Germany

[21] Appl. No.: 09/013,932

[22] Filed: Jan. 27, 1998

[30] Foreign Application Priority Data

Jan. 30, 1997 [DE] Germany .......................... 197 03 426

[51] Int. Cl.⁶ .............................. B01P 17/06; C07C 51/42
[52] U.S. Cl. ............................................ 210/748; 562/580
[58] Field of Search .............................. 562/580; 210/748

[56] References Cited

FOREIGN PATENT DOCUMENTS

95/08636  3/1995  WIPO .
WO97/10201  3/1997  WIPO .

OTHER PUBLICATIONS

Database WPIDS on STN, AN No. 94–000485, Habermann et al., 'Dicarboxylic acids and diamine(s) from polyamide(s)–by cleavage with alcoholic base solution, distilling diamine and converting solid salt into corresponding diacid by electrolysis.' abstract of DE 4219756, 1993.

*Chem. Berichte,* 119, pp. 2191–2207, 1986.

*J. Am. Chem. Soc.,* 77, p. 6008 (1955.).

*Primary Examiner*—Porfirio Nazario-Gonzalez
*Assistant Examiner*—Brian J. Davis
*Attorney, Agent, or Firm*—Keil & Weinkauf

[57] ABSTRACT

The process for purifying an α-, β- or γ-substituted carboxylic acid or a salt or an ester thereof or a mixture of two or more thereof from an aqueous solution which contains an α-, β- or γ-substituted carboxylic acid or a salt or an ester thereof or a mixture of two or more thereof and at least one polyol or at least one amino alcohol, wherein the solution is treated by electrodialysis.

19 Claims, 4 Drawing Sheets

PURIFICATION OF α-, β- OR γ-SUBSTITUTED CARBOXYLIC ACIDS

The invention relates to a process for purifying an α-, β- or γ-substituted carboxylic acid or a salt or an ester thereof or a mixture of two or more thereof from an aqueous solution, this solution containing at least one polyol or at least one amino alcohol, with or without a cation of a strong base, and being treated by electrodialysis, and to a process for cleaving an optically active amide and a process for resolving a mixture of two enantiomers of a primary or secondary amine, each of which comprise the purification process according to the invention as one stage.

The hydrolytic cleavage of optically active amides which have a center of chirality in the amine part of the molecule in such a way that the center of chirality is retained is possible only under very elaborate conditions, if at all.

BACKGROUND AND FIELD OF THE INVENTION

DESCRIPTION OF THE RELATED ART

Devant and Braun (Chem. Berichte 119 (1986) 2191–2207) describe the impossibility of eliminating chiral amines from acetamides without destroying the center of chirality (page 2194). The authors were furthermore unsuccessful in numerous attempts to hydrolyze the amides with alkali or acid to the carboxylic acid and optically active amine, and they found that the required result was achieved only by reaction with dinitrogen tetroxide as described by White (J. Am. Chem. Soc. 77 (1955) 6008). However, this reaction with $N_2O_4$ is elaborate and therefore unsuitable for industrial processes.

WO 95/08636 describes an enzymatic process for resolving optically active amines in which the amines are enantioselectively acylated with an ester, then the mixture of acylated amine (amide) and unreacted amine is separated and, where appropriate, the optically active amine is liberated from the acylated amine (amide) by amide cleavage. However, no possible parameters for the amide cleavage process are indicated.

As a continuation of this process, PCT/EP/96/03948 describes a process for cleaving optically active amides to carboxylic acids and optically active amines with retention of the center of chirality, which comprises hydrolyzing the amides in the presence of a polyol or amino alcohol and of an alkali metal or alkaline earth metal hydroxide.

The carboxylic acids employed in this case as auxiliary reagent for the enzymatic resolution of optically active amines are preferably α-, β- or γ-substituted carboxylic acids which are, as a rule, used as aqueous solution which, besides a salt or an ester of the above carboxylic acid, contains at least one polyol or at least one amino alcohol and an alkali metal or alkaline earth metal hydroxide. The solutions have hitherto always been fed to an incinerator.

Fractionation of a mixture of this type by distillation is usually impossible because the carboxylic acids or their salts or esters are able to react to esterify the polyol, eg. ethylene glycol (EG) or diethylene glycol (DEG), or the amino alcohol, eg. ethanolamine, diethanolamine and triethanolamine (TEA) and/or to form a salt (in the case of TEA). Accordingly, to optimize the yield, it is previously necessary to remove as far as possible the abovementioned components present besides the carboxylic acid or the salt or ester thereof. Workup by distillation is generally difficult or industrially very elaborate because of the high boiling points of the abovementioned compounds. It has also to be taken into account that ethylene glycol, for example, has a similar boiling point to many of the carboxylic acids under discussion here, eg. methoxyacetic acid, which in turn makes removal of the acid from the above mixture by distillation difficult.

BRIEF SUMMARY OF THE INVENTION

It is an object of the present invention to provide a relatively simple and economic process for purifying α-, β- or γ-substituted carboxylic acids from aqueous solutions.

We have found that this object is achieved by a process for purifying ("purification process" frequently hereinafter) an α-, β- or γ-substituted carboxylic acid or a salt or ester thereof or a mixture of two or more thereof from an aqueous solution which contains an α-, β- or γ-substituted carboxylic acid or a salt or an ester thereof and at least one polyol or at least one amino alcohol, with or without at least one cation of a strong base, wherein the solution is treated by electrodialysis.

The process according to the invention is particularly suitable for purifying an α-, β- or γ-substituted carboxylic acid or a salt thereof from distillation residues resulting from the resolution of a mixture of two enantiomers of a primary or secondary amine.

Accordingly, the process according to the invention for recovering the above-defined carboxylic acids by treatment by electrodialysis can also be employed as one stage in a process for cleaving an optically active amide to a carboxylic acid or a salt thereof and an optically active amine with retention of the center of chirality, or as one stage in a process for resolving a mixture of two enantiomers of a primary or secondary amine.

Processes of these types are described in PCT/EP/96/03948 and in WO 95/08636, the contents of which, in particular concerning the general conditions for carrying out the processes and the compounds and reagents preferably employed therein, are included in their entirety in the present application by reference.

The present invention thus also relates to a process for cleaving an optically active amide to a carboxylic acid or a salt thereof and an optically active amine with retention of the center of chirality, which comprises hydrolysis of the amide in the presence of at least one polyol or at least one amino alcohol and at least one cation of a strong base, the resulting α-, β- or γ-substituted carboxylic acid or the salt thereof being purified by the purification process according to the present invention, and to a process for resolving a mixture of two enantiomers of a primary or secondary amine which comprises the following steps:

1) Reacting the mixture of two enantiomers of the amine with an ester whose acid component has a halogen, nitrogen, oxygen, phosphorus or sulfur atom bonded to a carbon atom in the position α, β or γ to the carbonyl carbon atom, with specific catalysis by a hydrolase, (2) Separating one amine, which is enantioselectively acylated (amide), from the other, unreacted, enantiomer of the amine, (3) Subsequently hydrolyzing the acylated amine (amide) and purifying and recovering a corresponding α-, β- or γ-substituted carboxylic acid or a salt thereof by a purification process as defined above.

BRIEF DESCRIPTION OF THE DRAWINGS

FIG. 1 shows diagrammatically the resolving process according to the invention starting from a racemic primary aromatic amine;

FIG. 2 is a sketch of the principle of conventional dual cycle electrodialysis for the example of a sodium carboxylate;

FIG. 3 is a sketch of the principle of bipolar triple cycle electrodialysis for the example of a sodium carboxylate;

FIG. 4 is a sketch of the principle of bipolar dual cycle electrodialysis for the example of the fractionation of a sodium carboxylate and an alkanolamine.

Figure 1:
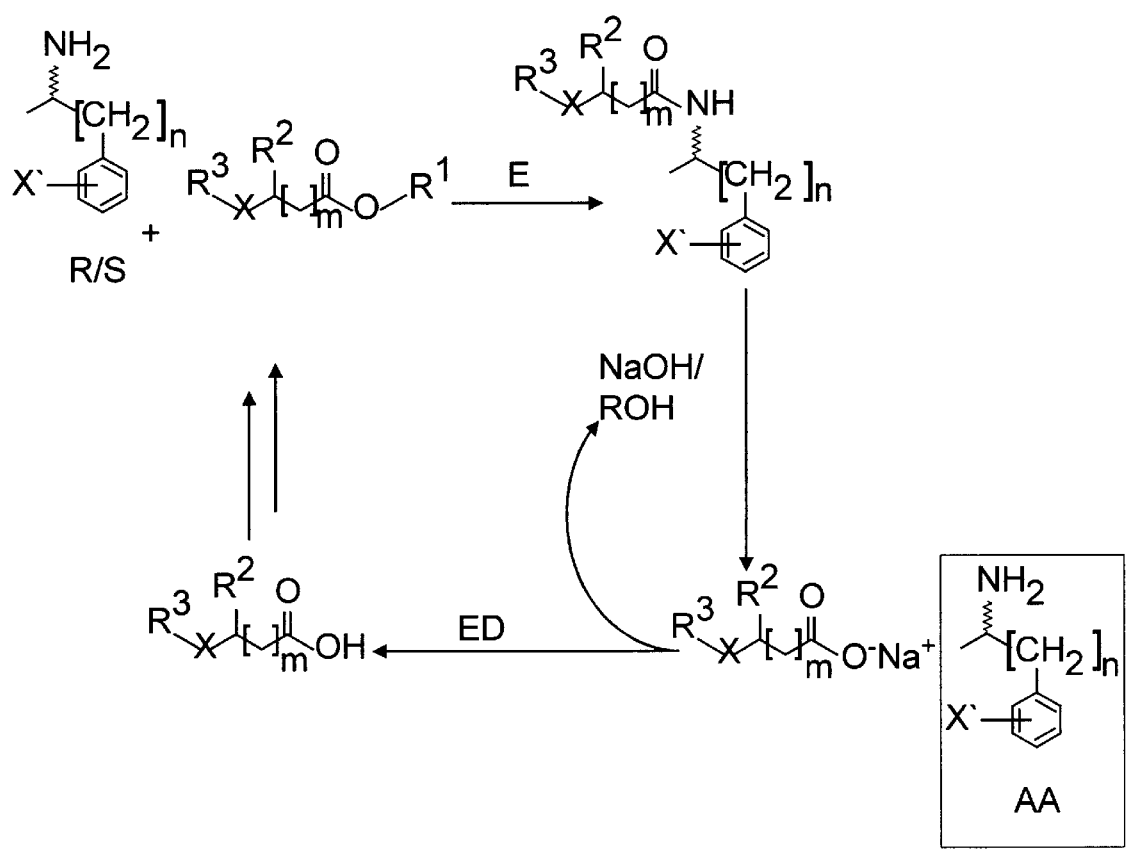
FIGS. 1 to 4 are appended for further illustration of the subject-matter of the application.

In the figures the used numerals and letters have the following meaning:

| (1) | diluate cycle |
|---|---|
| (2) | acid cycle |
| (3) | base cycle |
| (4) | concentrate cycle |
| A | anode |
| K | cathode |
| AM | anion exchange membrane |
| KM | cation exchange membrane |
| BM | bipolar membrane |
| E | enzyme |
| ED | electrodialysis |
| AA | R-amine (removal) |

DETAILED DESCRIPTION OF THE INVENTION

The process according to the invention for purifying an α-, β- or γ-substituted carboxylic acid or a salt or ester thereof or a mixture of two or more thereof (frequently also referred to as "carboxylic acid" hereinafter) from an aqueous solution as defined above is suitable in principle for purifying all carboxylic acids of this type where the substituents present in the position α, β or γ to the carboxyl group are preferably electron-rich heteroatoms such as a halogen, nitrogen, oxygen, phosphorus or sulfur atom, especially oxygen.

The heteroatom may, where appropriate, be linked to other groups such as alkyl groups.

Particularly suitable carboxylic acids or their salts or their esters have a structure of the formula (I)

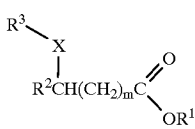

where $R^1$ is hydrogen, $C_1$–$C_{10}$-alkyl or an alkali metal ion, preferably $Na^+$ or $K^+$, $R^2$ is $C_1$–$C_{10}$-alkyl or hydrogen, $R^3$ is hydrogen, $C_1$–$C_{10}$-alkyl, or phenyl which is unsubstituted or substituted by $NH_2$, OH, $C_1$–$C_4$-alkyl or $C_1$–$C_4$-alkoxy or halogen, X is a halogen atom, preferably fluorine (no $R^3$ present), nitrogen, oxygen, phosphorus or sulfur, especially oxygen, and m is 0, 1 or 2.

The compounds covered by the above structural formula which are preferably employed are $C_1$–$C_4$-alkoxy derivatives of lower carboxylic acids such as methoxy- or ethoxyacetic acid, methoxy- or ethoxypropionic acid and methoxy- or ethoxybutyric acid, and their salts, for example sodium methoxy acetate, sodium methoxypropionate or sodium methoxybutyrate, with further preference for methoxyacetic acid or a salt thereof, especially its sodium salt. The esters preferably employed are the methyl, ethyl, propyl or n-, sec- or tert-butyl esters of the abovementioned acids.

The components preferably present in the solutions to be purified, besides the carboxylic acid defined above or its salt or ester, as the at least one polyol or the at least one amino alcohol and, where appropriate, as the at least one cation of a strong base, correspond to the polyols, amino alcohols and alkali metal or alkaline earth metal hydroxides described in detail in PCT/EP/96/03948. However, as a rule, the solutions to be purified, especially when the solutions are obtained directly from the processes disclosed in WO 95/08636 and the process described in PCT/EP/96/03948, contain ethylene glycol or diethylene glycol as polyol, ethanolamine or diethanolamine as amino alcohol, and sodium and/or potassium ions from sodium and/or potassium hydroxide as cations of a strong base.

The term "cations of a strong base" comprises all cations derived from bases which are substantially dissociated in the solutions under discussion here. Cations which should be mentioned as preferred in this connection are those derived from bases with a $pK_B$ of 0±3.5. Particular mention should be made of alkali metal and/or alkaline earth metal cations (from alkali metal and/or alkaline earth metal hydroxides) and $NR'_4^+$ cations, where the R' groups are identical or different and each is hydrogen or alkyl, especially methyl. However, the solutions to be treated in the purification process according to the invention, eg. distillation residues from the processes described above for resolving a mixture of two enantiomers of a primary or secondary amine, or for cleaving optically active amides to carboxylic acids and optically active amines with retention of the center of chirality, not uncommonly result in a form which cannot be directly subjected to electrodialysis.

These solutions are often high viscous and contain constituents which may damage the membranes used in the electrodialysis.

Accordingly, crude solutions of this type must undergo a working up such as a dilution, distillation, filtration or else selective ion exchange before being used in the process according to the invention.

When anion exchange membranes (AM) are used in electrodialysis, it is as a rule necessary, because of the alkali lability of these membranes, to neutralize the excess NaOH which is present in the solutions where appropriate and to adjust the pH to approximately 10. When the alkali-stable AMs, which have been commercially available for some years, eg. AMH (Tokuyama Corp.) and AMP (Asahi Glass), are used, it is possible to dispense with such an adjustment of the pH where appropriate. However, even when these membranes are used, a pH adjustment as defined above is preferably carried out. The acids which can be used for this neutralization are all those able to pass through a membrane and be separated from the above-defined carboxylic acids by distillation, such as formic acid.

The concentration of the carboxylic acid in the aqueous solutions employed in the purification process according to the invention is approximately 5 to approximately 30, preferably approximately 5 to approximately 25 and, in particular, approximately 5 to approximately 15, % by weight. The content of polyol or amino alcohol is generally approximately 35 to approximately 85, preferably approximately 45 to approximately 85 and, in particular, approximately 15 to approximately 40, % by weight. The water content in the solution employed according to the invention is generally approximately 40 to approximately 80% by weight, and the content of base, preferably alkali metal or alkaline earth metal hydroxide, is (if present) generally approximately 0.5 to approximately 5% by weight.

For the purpose of the present invention, the electrodialysis is carried out as conventional dual cycle electrodialysis, bipolar dual cycle electrodialysis or bipolar triple cycle electrodialysis or a combination of two or more thereof.

Where the aqueous solution to be worked up contains, besides the α-, β- or γ-substituted carboxylic acid or a salt or an ester thereof, at least one polyol and at least one cation of a strong base, it is preferably treated initially by conventional dual cycle electrodialysis and subsequently by bipolar triple cycle electrodialysis. This entails, in the conventional dual cycle electrodialysis, an initial reduction in the concentration of the carboxylic acid or the salt or the ester thereof present in the aqueous solution, with the polyol substantially remaining in the diluate cycle, and a concentrate containing the carboxylic acid or its salt being obtained. The concentrate thus obtained is introduced as diluate into the 3-cycle electrodialysis, where further removal of the polyol takes place, and the salt of the carboxylic acid is cleaved to base and free carboxylic acid. A diagrammatic depiction of the two variants is shown in FIGS. 2 and 3 which will be explained in detail later.

Where the aqueous solution to be worked up contains, besides the abovementioned carboxylic acid or a salt or an ester thereof, an amino alcohol and a cation of a strong base, it is preferably treated by bipolar dual cycle electrodialysis.

Conventional dual cycle electrodialysis is known per se and is described in EP-B-0 381 134, whose contents relating to conventional dual cycle electrodialysis are included in their entirety in the present application.

Figure 2:
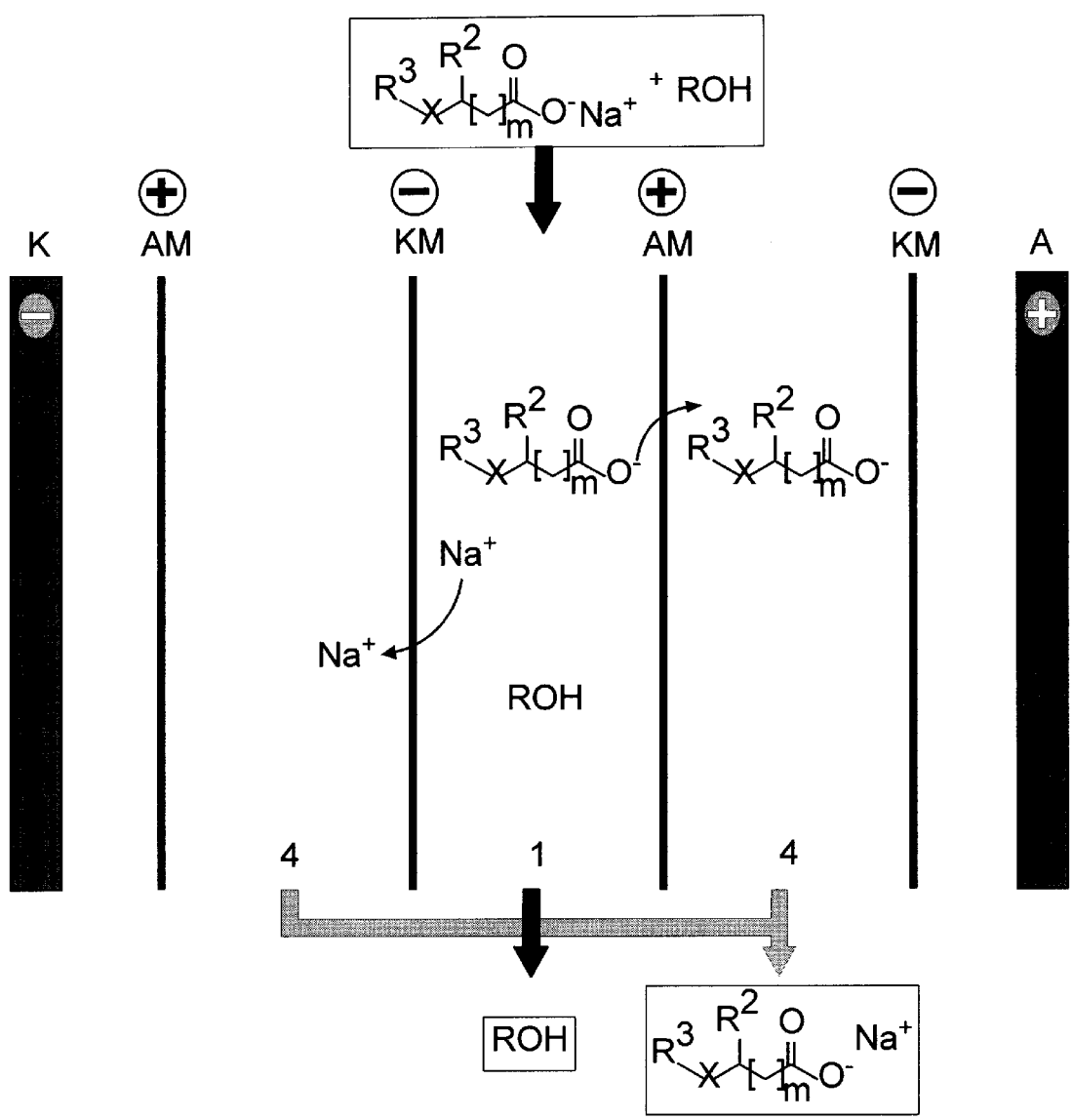
Figure 3:
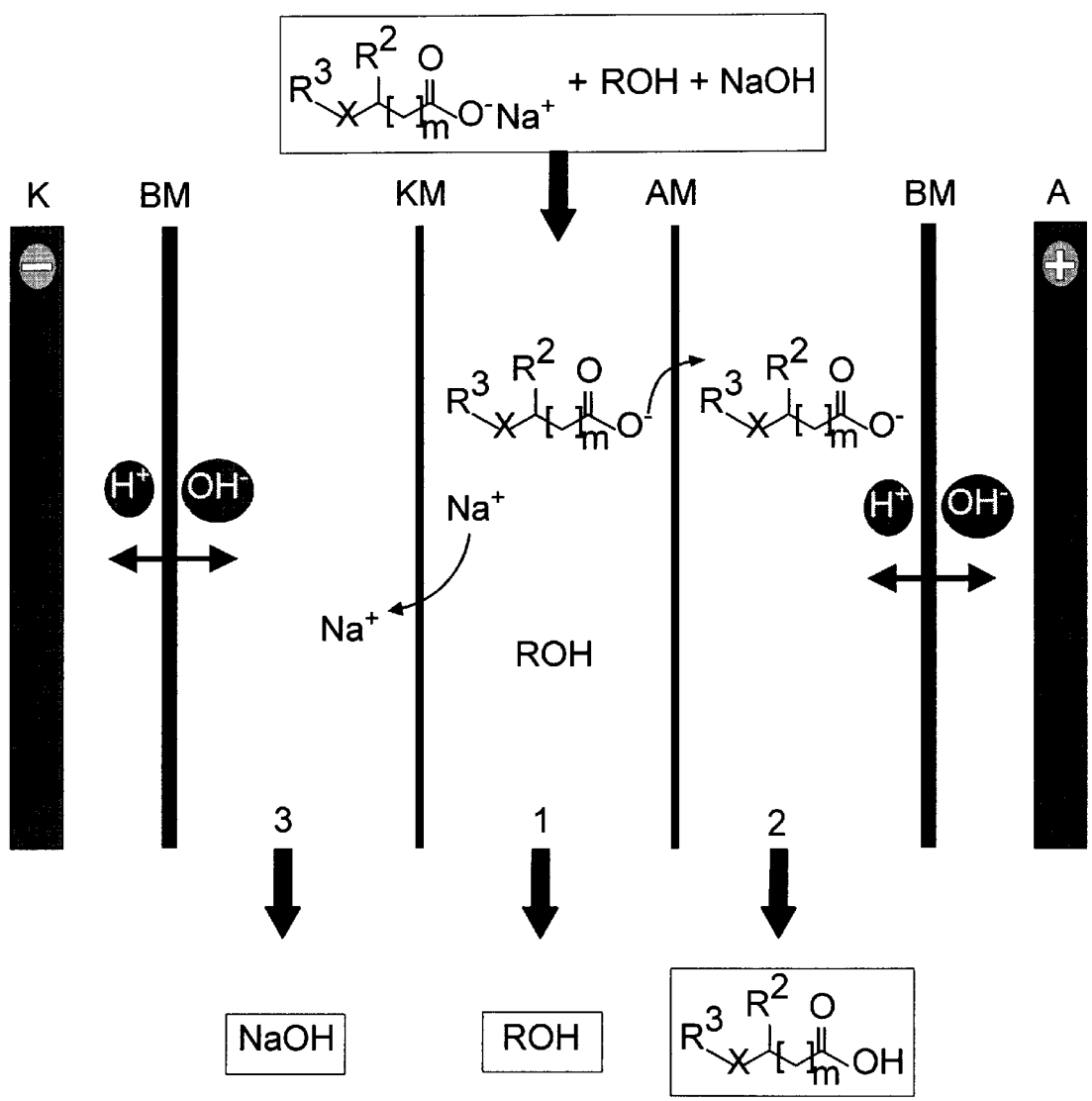

A sketch of the principle of this electrodialysis is shown in FIG. 2.

The apparatus employed in this variant of electrodialysis has a positive (anode (A)) and negative (cathode (K)) as large-area electrodes. The space between the electrodes is divided up by a large number of alternately arranged cation (KM) and anion (AM) exchange membranes in a large number of narrow chambers which are separated from one another by the membranes and which are also referred to as diluate cycle (1) and concentrate cycle (4). In this arrangement chambers which have an anion exchange membrane on the cathode side and a cation exchange membrane on the anode side are called concentrate chambers or concentrate cycles, while chambers which have the anion exchange membrane on the anode side and the cation exchange membrane on the cathode side form the diluate chambers or the diluate cycle.

To carry out the process according to the invention, the diluate cycles are filled with the aqueous solution to be purified, for example containing an Na salt of a carboxylic acid (II) where m, X, $R^2$ and $R^3$ are defined as for structure (I), and an amino alcohol or a polyol represented by ROH, and the concentrate cycles are filled with an aqueous electrolyte. The chambers in which the electrodes are located and, where appropriate, also the chambers directly adjacent thereto are charged with an electrode rinsing solution, usually a sodium sulfate solution.

Under the influence of the voltage applied to the electrodes, the ions migrate through the membrane which is permeable to them from the diluate cycle into the concentrate cycle. Further migration through the following membrane which is impermeable to the relevant type of ions is impossible, and the ion remains in the concentrate cycle. The liquids in the diluate, concentrate and electrode cycles are separately circulated by pump, where appropriate with interpolated reservoirs.

As a modification of the conventional dual cycle electrodialysis disclosed in EP-B0 381 134, it is also possible to employ a membrane arrangement using bipolar membranes. Bipolar membranes are laminates of anion and cation exchange membranes. They are distinguished from monopolar anion and cation exchange membranes by efficiently catalyzing water cleavage in the electric field for the electrodialysis, and thus also serve to provide $H^+$- and $OH^-$ equivalents.

The properties of the bipolar membranes can be used in the manner depicted in FIG. 3 to obtain pure acid. The mode of functioning is described briefly below once again on the basis of the treatment of an aqueous solution of an Na salt of a carboxylic acid of structure (II) and a polyol or amino alcohol ROH as explained in each case with reference to FIG. 2.

A triple cycle (chamber) arrangement (bipolar triple cycle electrodialysis) consisting of diluate (1), acid (2) and base (3) cycles is used. The triple cycle arrangement is achieved by an alternating sequence of the particular exchange membranes:

| ... BM | BC | KM | DC | AM | AC | BM ... |
|--------|----|----|----|----|----|--------|

KM=cation exchange membrane; BM=bipolar membrane;

AM=anion exchange membrane;

BC=base cycle; AC=acid cycle; DC=diluate cycle

The aqueous solution which is to be fractionated and contains the carboxylic acid or its salt or ester and the solvent is fed into the diluate cycle. A dilute carboxylic acid solution (eg. 0.5% strength) is introduced into the acid cycle, while an appropriately diluted base, eg. NaOH, is introduced into the base cycle. When the electrodialysis current is switched on, as in conventional electrodialysis there is migration of cations (for example $Na^+$) from the diluate cycle into the base cycle, while the acid anion migrates into the acid cycle. The base (NaOH) and the α-, β- or γ-substituted carboxylic acid are generated respectively in the base and acid cycles with the $OH^-$ and $H^+$ ions from the simultaneous water cleavage by the bipolar membrane.

Figure 4:
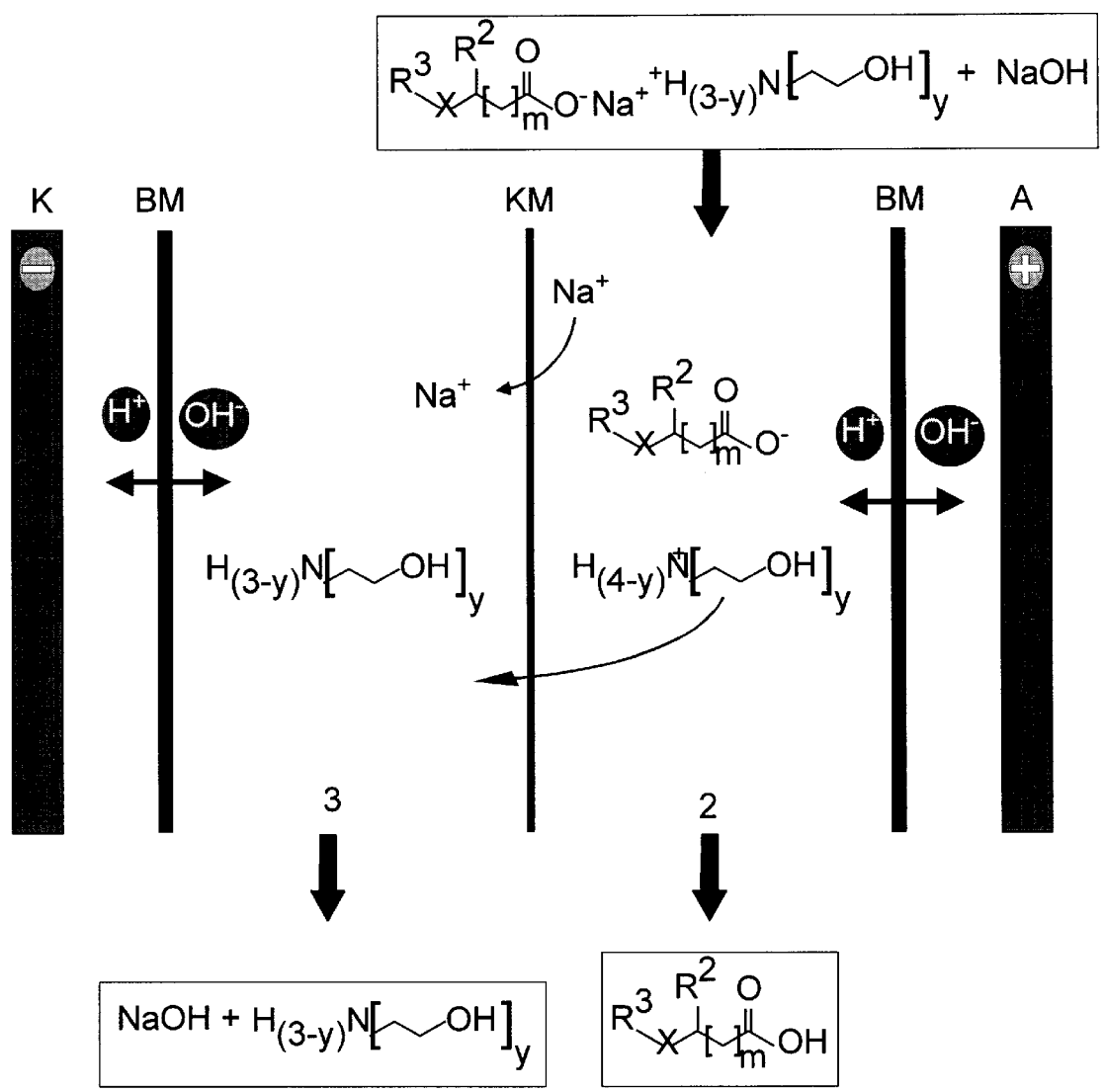

If an alkanolamine is present in the solution, a bipolar dual cycle electrodialysis is preferably employed in addition to the bipolar triple cycle electrodialysis. An arrangement of this type is shown in FIG. 4 and consists of base (3) and acid (2) cycles. This arrangement is achieved by an alternating sequence of the relevant ion exchange membranes:

| ... BM | BC | KM | AC | BM ... |
|--------|----|----|----|--------|

BM=bipolar membrane; KM=cation exchange membrane;

BC=base cycle; AC=acid cycle

In this arrangement, the solution to be treated according to the invention is employed in the acid cycle, and a highly diluted solution of a base (eg. 0.5% strength NaOH) is introduced into the base cycle. When the electrodialysis current is switched on there is likewise migration of the positively charged ions through the cation exchange membrane from the acid cycle into the base cycle, and the corresponding bases are formed there with the OH⁻ ions from the water cleavage emerging from the bipolar membrane. The anions remain in the acid cycle and form the corresponding free acid with the H⁺ ions present therein. Further details are to be found, for example, in K. N. Mani, J. Membr. Sci. 58 (1991), 117–38.

The nomenclature of the compounds employed in this case corresponds to what has been said on FIGS. 1 and 2, and y can—as additional variable—assume the values 0, 1, 2, 3, 4.

The process according to the invention is preferably carried out at approximately 10 to approximately 50° C., in particular from approximately 20 to approximately 30° C. The current density in conventional dual cycle electrodialysis varies from 100 to 700 A/m², preferably from 50 to 500 A/m². In bipolar triple cycle electrodialysis, the current density varies from 1 to 2,000 A/m², preferably from 500 to 1,500 A/m². These figures also apply to bipolar dual cycle electrodialysis.

Commercial ion exchange membranes are employed in the electrodialysis carried out for the purpose of the present process.

These preferably consist of organic polymers having ionic side chains. Cation exchange membranes contain sulfonate or carboxyl groups in the polymer matrix, while anion exchange membranes have tertiary or quaternary amino groups as substituents of the polymeric base material. Copolymers of styrene and divinylbenzene are particularly suitable as polymeric base material for the ion exchange membranes. Examples of anion exchange membranes which can be used are: Tokuyama AM1, AM2, AM3, AMX, AMH, AFN, Asahi Glass AMP, AMV. Examples of cationic exchange membranes which may be mentioned are Tokuyama CM1, CM2, CMX, CMH and Asahi Glass CMV. Examples which may be mentioned of bipolar membranes are Tokuyama BP1 and Aqualytics Membranes.

Because anion exchange membranes are, as already described above, alkali-labile, the preferred embodiments of the present process are those in which it is possible to dispense with use of anion exchange membranes.

As a rule, it is possible in the process according to the invention to achieved by a single electrodialysis a decrease in the solvent concentration (decrease in polyol/amino alcohol concentration) of approximately 80%, preferably up to about 90%, in each case based on the initial content. This is achieved as a rule on use of relatively dilute initial solutions containing the carboxylic acid in a concentration of from 5 to 15% by weight.

As an alternative to this, the solutions are subjected in the process according to the invention to a double electrodialysis in which more concentrated initial solutions which, as already mentioned above, may have a content of carboxylic acid or a salt thereof of up to 30% by weight are also processed. It is possible by this double electrodialysis to reduce the solvent concentration by up to 95%.

Since, as mentioned above, the ratio of the amounts of carboxylic acid and solvent in the concentrate cycle/acid cycle can reach approximately 15:1 after a single electrodialysis in the most favorable case, and traces of solvent in the concentrate are still to be expected even after double electrodialysis, it must be assumed that losses of yield due to the formation of products of low solubility from reactions between the solvent and carboxylic acid, such as involatile mono-, di- or triesters, will occur in the distillation which usually follows the process according to the invention to remove the carboxylic acid, leading to losses of yield of carboxylic acid.

Accordingly, in another embodiment of the present invention, the bottom product from the distillation carried out after the electrodialysis in the purification process according to the invention is mixed with a stoichiometric amount of dilute base (for example 3.5% strength sodium hydroxide solution), which usually leads to complete ester cleavage to form a salt of the required carboxylic acid and of the polyol or amino alcohol, that is to say, for example, the formation of sodium methoxy acetate and ethylene glycol. The mixture obtained in this way can then be fed into an electrodialysis once again together with fresh solution.

This variant of the process according to the invention represents an alternative to treating the solution which is to be purified twice by electrodialysis.

In any event, this alternative makes it possible to accept a significant residual content of polyol or amino alcohol before the concluding distillation.

In another embodiment of the present invention, the aqueous solution is passed, during the electrodialysis or after passing through the electrodialysis, through a cation exchange module in order to achieve a further reduction in the concentration of solvent and further purification of the carboxylic acid.

The moment at which electrodialysis is coupled to a cation exchange process is chosen so that the main reduction in the concentration of cations by electrodialysis has already taken place.

The "switching on" of the cation exchange process normally takes place when a defined conductivity is reached in the electrodialysis diluate and correlates with a reduction in the base concentration of 80 to 99%, preferably 90 to 99%, ie. the electrodialysis is preferably coupled to a cation exchange process on reaching a conductivity of approximately 20 mS/cm or less, further preferably at a conductivity of approximately 10 mS/cm or less and, in particular, at a conductivity of approximately 5 mS/cm or less.

Thus, in this variant of the process according to the invention, the electrodialysis is preferably initially operated until the conductivity of the diluate is approximately 20 mS/cm or less, and subsequently the diluate obtained in the electrodialysis is passed through a cation exchange module.

The process according to the invention can further be carried out in such a way that initially the electrodialysis is operated on its own until the conductivity of the diluate is approximately 20 mS/cm or less, and subsequently the diluate is both subject to the electrodialysis and passed through a cation exchange module.

Cation exchange modules which can be employed in the cation exchange process are devices, such as a column, which are packed with the cation exchangers described above with reference to the electrodialysis in the form of powders, beads, granules etc. In principle, all polymer-based cation exchangers are suitable, ie. both weakly and strongly acid cation exchangers. Examples which maybe mentioned are Dowex 50 W types, Amberlite IR 120 and IR 400, Lewatit S 100 and Duolite C 26.

In another embodiment of the process according to the invention, an α-, β- or γ-substituted carboxylic acid or a salt thereof in the form of an aqueous solution obtained in the resolution of an optically active amide to give a carboxylic acid and an optically active amide with retention of the center of chirality is purified according to the invention.

Thus, the process according to the invention can also be used as constituent of the process for cleaving optically active amides to carboxylic acids and optically active amines with retention of the center of chirality as described in PCT/EP/96/03948 or as constituent of the process described in WO 95/08636 for resolving a mixture of two enantiomers of a primary or secondary amine.

FIG. 1 summarizes the overall process taking the example of an aromatic amine of the following structure

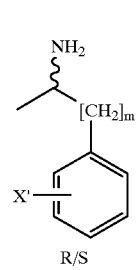

(II)

where X' is conventional substituents for aromatic compounds, especially halogen, linear and branched alkyl groups having 1–6 carbon atoms, linear alkoxy groups having 1–6 carbon atoms, acyl groups having 1–6 carbon atoms, and cyano groups, and n assumes the values 1, 2, 3, 4, 5, 6, etc.

In this overall process, firstly the mixture of two enantiomers of a primary or secondary amine with an ester whose acid component has a halogen, nitrogen, oxygen, phosphorus or sulfur atom bonded to a carbon atom in the position α, β or γ to the carbonyl carbon is converted, with specific catalysis by a hydrolase, into the two enantiomeric forms.

Suitable esters are the esters already described above in detail and covered by formula (I).

The hydrolases which can be used are likewise described in detail in WO 95/08636 and are included herein merely by reference to this document.

In another step, one amine, which is enantioselectively acylated (amide), is separated from the other, unreacted, enantiomer of the amine, for example by fractional distillation.

The optically active amide obtained is subsequently cleaved to a carboxylic acid and an optically active amine with retention of the center of chirality, the hydrolysis being carried out in the presence of at least one polyol or at least one amino alcohol and at least one cation of a strong base.

Suitable polyols and amino alcohols in this case are the polyols and amino alcohols likewise mentioned at the outset and described in WO 95/08636.

The amine liberated during the hydrolysis is removed by distillation, and the solution obtained in this way and containing a carboxylic acid substituted in position α, β or γ, at least one polyol or at least one amino alcohol and at least one alkali or earth alkali hydroxide [lacuna] is subjected to the purification process according to the invention.

The carboxylic acid or the salt thereof which is finally obtained in the purification process according to the invention can then in turn be esterified and added as esterifying agent to the reaction of the racemic amines.

EXAMPLES

1. Conventional Electrodialysis

General Conditions

Conventional electrodialysis was carried out in a 2-cycle electrodialysis module with an alternating arrangement of cation and anion exchange membranes (see FIG. 2), using Tokuyama AM3 anion exchange membranes and CM2 cation exchange membranes. The membranes were arranged with a spacing of 0.5 mm apart.

The module was composed of 5 diluate and 5 concentrate chambers, which corresponded to an effective total membrane area of 3.78 dm$^2$. Platinated titanium electrodes were employed as anode and cathode materials. The nominal current density was 5.3 A/dm$^2$, and the maximum voltage drop per cell (1 diluate and concentrate chamber pair) was limited to 2V. The electrodialysis temperature was 40° C.

Example 1

800 g of an aqueous solution consisting of sodium methoxyacetate (NaMes) (20.9%) and ethylene glycol (EG) (34.9%) were employed in the diluate cycle, corresponding to an NaMes/EG molar ratio of y≈0.3.

500 g of a 2% strength aqueous sodium methoxyacetate solution were introduced into the concentrate cycle. The electrolyte cycle was filled with a 5% strength aqueous sodium sulfate solution.

The transfer of sodium and methoxyacetate ions into the concentrate cycle was stopped after 5 h by switching off the rectifier. 778 g of concentrate discharge of the following composition were obtained:

NaMes 18.23%; EG 2.78%; y≈3.6.

Example 2

As a modification of Example 1, 1200 g of an aqueous diluate solution of the following composition were employed:

NaMes 14.0%; EG 23.5%; y≈0.3.

After electrodialysis for 5 h, 845 g of concentrate of the following composition were obtained:

NaMes 17.1%; EG 1.4%; y≈6.8.

Example 3

As a modification of Example 1, 2400 g of an aqueous diluate solution of the following composition were employed:

NaMes 7.0%; EG 11.63%; y≈0.3.

After electrodialysis for 5 h, 917 g of concentrate of the following composition were obtained:

NaMes 15.7%; EG 0.6%; y≈14.4.

Example 4

845 g of concentrate discharge (from Example 2; see above for composition) were subjected anew to electrodialysis as initial diluate.

After electrodialysis for 5 h, 752 g of concentrate of the following composition were obtained:

NaMes 16.2%; EG<0.05%; y≈18.0.

2. Bipolar Electrodialysis (3-cycle)

General Conditions

The bipolar 3-cycle electrodialysis was carried out with an alternating arrangement of the following membranes:

Bipolar membrane (Aqualytics, USA)—anion exchange membrane (AM3, Tokuyama Corp., JP)—cation exchange membrane (CM2, Tokuyama Corp., JP). The membranes were arranged at a spacing of 1.0 mm apart.

The module consisted of 5 diluate, 5 acid and 5 base chambers, corresponding to a total active membrane area of 27 dm$^2$. Nickel was used as anode material and stainless steel was used as cathode material. The nominal current density was 8.0 A/dm$^2$, and the maximum voltage drop per cell (segment consisting of acid, diluate, and base cycles) was limited to 4.0

V. The electrodialysis temperature was 40° C.

Example 5
Initial Specification of the Solutions Employed
a) 2400 g of diluate cycle of the following composition: NaMes 14.0%; EG 23.3%; y≈0.3.
b) 800 g of acid cycle of the following composition: methoxyacetic acid/HMes, aqueous 2.0%.
c) 1000 g of base cycle of the following composition: sodium hydroxide, aqueous 2.0%.
d) 1000 g of electrolyte cycle of the following composition: sodium hydroxide, aqueous 6.0%.

After 70 minutes the transfer of methoxyacetate ions and sodium ions from the diluate into the acid and base cycles, respectively, was stopped by switching off the rectifier. The following electrolyte analysis discharges were obtained:
a) 1808 g of diluate cycle of the following composition: NaMes 1.9%; EG 25.4%; y≈0.04.
b) 1141 g of acid cycle of the following composition: HMes, 21.5%; EG 1.7%; y≈7.0.
c) 1242 g of base cycle of the following composition: sodium hydroxide, 8.7%.

The methoxyacetic acid (HMes) obtained in the acid cycle was isolated by simple vacuum distillation after the excess water had been stripped off.

3. Bipolar Electrodialysis (2-cycle)
General Conditions

The bipolar 2-cycle electrodialysis was carried out with an alternating arrangement of the following membranes: bipolar membrane (Aqualytics USA), cation exchange membrane (CMX, Tokuyama Corp. JP). The membranes were arranged at a spacing of 1.0 mm apart.

The module consisted of 5 acid and 5 base chambers, corresponding to a total active membrane area of 9.29 $dm^2$. Nickel was used as anode material and stainless steel was used as cathode material. The nominal current as density was 8.0 $A/dm^2$, and the maximum voltage drop per cell (segment consisting of acid and base cycles was limited to 3.5 V. The electrodialysis temperature was 40° C.

Example 6
Initial Specification of the Solutions Employed
a) 3000 g of acid cycle of the following composition: triethanolamine/TEA 27.3%; NaMes 17.0% (NaMes/TEA molar ratio of y≈0.83); NaOH 1.6%;
b) 2500 g of base cycle of the following composition: sodium hydroxide, aqueous 2.0%.
c) 1000 g of electrolyte cycle of the following composition: sodium hydroxide, aqueous 6.0%.

The transfer of triethanolammonium and sodium ions from the acid cycle into the base cycle was stopped after 590 min. when the pH of the acid cycle reached 1.7 by switching off the rectifier. The following electrodialysis discharges were obtained:
a) 822 g of acid cycle of the following composition: TEA 1.1%; HMes 30.7%; y≈46.
b) 4650 g of base cycle of the following composition: TEA 15.0%; NaMes 2.9%; NaOH 3.3%.

The acid cycle discharge was concentrated in a rotary evaporator by stripping off 546 g of water (bath temperature 60° C.; 30 mbar). The residue of 276 g was subjected to a simple vacuum distillation (bottom temp. 70–130° C.; 0.3→0.01 mbar). Four HMes fractions corresponding to a total amount of HMes of 227.9 g=90.3% of theory were obtained. Fractions 3 and 4 (214.3 g of HMes=85% of theory) were returned with a purity of ≧99.0% to the enzymatic resolution. Fractions 1 and 2 were fed into the distillation batch of a following test.

The base cycle discharge was used for a renewed amide cleavage.

24 g of organic/salt-containing distillation residue were left for disposal.

Example 7
a) 3000 g of acid cycle of the following composition: triethanolamine/TEA 19.3%; NaMes 12.3% (NaMes/TEA molar ratio of y≈0.85); NaOH 1.0%.
b) 2500 g of base cycle of the following composition: sodium hydroxide, aqueous 2.0%.
c) 1000 g of electrolyte cycle of the following composition: sodium hydroxide, aqueous 6.0%.

The transfer of triethanolammonium and sodium ions from the acid cycle into the base cycle was stopped after 426 min. when the pH of the acid cycle reached 2.4 by switching off the rectifier. The following electrodialysis discharges were obtained:
a) 1500 g of acid cycle of the following composition: TEA 2,15%; total Mes 17.0% (calc. HMes distributed over liberated carboxylic acid =15.7% and TEA/Na methoxyacetate 1.3%); y≈12.
b) 4050 g of base cycle of the following composition: TEA 13.4%; NaMes 1.1%; NaOH 2.8%.

The acid cycle discharge was concentrated in a rotary evaporator by stripping off 1011 g of water (bath temperature 60° C.; 30 mbar). The residue of 489 g was subjected to a simple vacuum distillation (bottom temp. 70–140° C.; 0.3–0.01 mbar). Four HMes fractions corresponding to a total amount of HMes of 199.7 g were obtained. These contained 84.8% of the HMes present in the acid cycle discharge and 78.3% of the methoxyacetate present in the acid cycle discharge. Fractions 3 and 4 (178.7 g of HMes= 75.9/70.1% of theory) were combined and contained HMes with a purity of ≧95.8%. Fractions 1 and 2 were returned to the distillation in a following test.

The base cycle discharge was used for a renewed amide cleavage.

72 g of organic/salt-containing distillation residue were left for disposal.

Example 8

The electrodialysis procedure corresponded to the statements in Example 7. As a modification of Example 7, 1500 g of acid cycle discharge with a similar composition were deionized, on a column packed with a strongly acidic cation exchanger (Amberlite IR120/$H^+$, ≈250 ml; diameter 40 mm, bed height 200 mm). The collected ion exchange eluate (≈2250 g) was concentrated by stripping off water in a rotary evaporator (bath temp. 60° C.; 30 mbar). The residue of 257 g was subjected to a simple vacuum distillation (bottom temp. 70–130° C.; 0.3→0.01 mbar). Two HMes fractions corresponding to a total amount of HMes of 246.1 g were obtained. These contained 96.5% of the methoxyacetic acid present in the acid cycle discharge in the form of salt/acid. Fractions 1 and 2 were combined and contained HMes with a purity ≧99.0%. They were returned to the enzymatic resolution.

The base cycle discharge was used for renewed amide cleavage.

1.5 g of organic/salt-containing distillation residue were left for disposal.

We claim:

1. A process for purifying an α-, β- or γ-substituted carboxylic acid or a salt or an ester thereof or a mixture of two or more thereof from an aqueous solution which contains an α-, β- or γ-substituted carboxylic acid or a salt or an ester thereof or a mixture of two or more thereof and at least one polyol or at least one amino alcohol, wherein the solution is treated by electrodialysis.

2. A process as claimed in claim 1, wherein the aqueous solution additionally contains at least one cation of a strong base.

3. A process as claimed in claim 1, wherein the electrodialysis is carried out as conventional dual cycle electrodialysis, bipolar dual cycle electrodialysis or bipolar triple cycle electrodialysis or as combination of two or more thereof.

4. A process as claimed in claim 2, wherein the aqueous solution contains at least one polyol and at least one cation of a strong base and is treated firstly by conventional dual cycle electrodialysis and subsequently by bipolar triple cycle electrodialysis.

5. A process as claimed in claim 2, wherein the aqueous solution contains at least one amino alcohol and at least one cation of a strong base and is treated by bipolar dual cycle electrodialysis.

6. A process as claimed in claim 1, wherein the aqueous solution is passed through a cation exchange module during the electrodialysis or after passing through the electrodialysis.

7. A process as claimed in claim 2, wherein the aqueous solution is passed through a cation exchange module during the electrodialysis or after passing through the electrodialysis.

8. A process as claimed in claim 1, wherein the α-, β- or γ-substituted carboxylic acid or a salt thereof is in the form of an aqueous solution which has been obtained in the resolution of an optically active amide to give a carboxylic acid and an optically active amine with retention of the center of chirality.

9. A process as claimed in claim 2, wherein the α-, β- or γ-substituted carboxylic acid or a salt thereof is in the form of an aqueous solution which has been obtained in the resolution of an optically active amide to give a carboxylic acid and an optically active amine with retention of the center of chirality.

10. A process as claimed in claim 1, wherein the α-, β- or γ-substituted carboxylic acid or the salt thereof is methoxyacetic acid or a salt thereof.

11. A process as claimed in claim 2, wherein the α-, β- or γ-substituted carboxylic acid or the salt thereof is methoxyacetic acid or a salt thereof.

12. A process for cleaving an optically active amide to a carboxylic acid or a salt thereof and an optically active amine with retention of the center of chirality, which comprises hydrolysis of the amide in the presence of at least one polyol or at least one amino alcohol and at least one cation of a strong base, the resulting α-, β- or γ-substituted carboxylic acid or the salt thereof being purified by a process as claimed in claim 1.

13. A process for cleaving an optically active amide to a carboxylic acid or a salt thereof and an optically active amine with retention of the center of chirality, which comprises hydrolysis of the amide in the presence of at least one polyol or at least one amino alcohol and at least one cation of a strong base, the resulting α-, β- or γ-substituted carboxylic acid or the salt thereof being purified by a process as claimed in claim 2.

14. A process for resolving a mixture of two enantiomers of a primary or secondary amine which comprises the following steps:
  (1) Reacting the racemic mixture of two enantiomers of the amine with an ester whose acid component has a halogen, nitrogen, oxygen, phosphorus or sulfur atom bonded to a carbon atom in the position α, β or γ to the carbonyl carbon atom, with specific catalysis by a hydrolase,
  (2) Separating one amine, which is enantioselectively acylated (amide), from the other, unreacted, enantiomer of the amine,
  (3) Subsequently hydrolyzing the acylated amine (amide) and purifying and recovering a corresponding α-, β- or γ-substituted carboxylic acid or a salt thereof by a process as defined in claim 11.

15. A process for resolving a mixture of two enantiomers of a primary or secondary amine which comprises the following steps:
  (1) Reacting the racemic mixture of two enantiomers of the amine with an ester whose acid component has a halogen, nitrogen, oxygen, phosphorus or sulfur atom bonded to a carbon atom in the position α, β or γ to the carbonyl carbon atom, with specific catalysis by a hydrolase,
  (2) Separating one amine, which is enantioselectively acylated (amide), from the other, unreacted, enantiomer of the amine,
  (3) Subsequently hydrolyzing the acylated amine (amide) and purifying and recovering a corresponding (α-, β- or γ-substituted carboxylic acid or a salt thereof by a process as defined in claim 12.

16. A process as claimed in claim 14, wherein phenylethylamine is employed as amine.

17. A process as claimed in claim 15, wherein phenylethylamine is employed as amine.

18. A process as claimed in claim 14, wherein the purified and recovered α-, β- or γ-substituted carboxylic acid or the salt thereof is esterified and returned to the reaction of the mixture of two enantiomers of the amine.

19. A process as claimed in claim 15, wherein the purified and recovered α-, β- or γ-substituted carboxylic acid or the salt thereof is esterified and returned to the reaction of the mixture of two enantiomers of the amine.

* * * * *